(12) United States Patent
Osypka (10) Patent No.: US 8,219,195 B2
(45) Date of Patent: Jul. 10, 2012

(54) METHOD AND APPARATUS FOR AUTOMATIC DETERMINATION OF HEMODYNAMICALLY OPTIMAL CARDIAC PACING PARAMETER VALUES

(75) Inventor: Markus Osypka, Knuellwald (DE)

(73) Assignee: Osypka Medical GmbH, Berlin (DE)

( * ) Notice: Subject to any disclaimer, the term of this patent is extended or adjusted under 35 U.S.C. 154(b) by 1003 days.

(21) Appl. No.: 11/956,669

(22) Filed: Dec. 14, 2007

(65) Prior Publication Data

US 2008/0103541 A1 May 1, 2008

Related U.S. Application Data

(62) Division of application No. 10/402,230, filed on Mar. 27, 2003, now abandoned.

(30) Foreign Application Priority Data

Apr. 3, 2002 (EP) ..................................... 02007574

(51) Int. Cl.
*A61N 1/365* (2006.01)
(52) U.S. Cl. ........................................................ 607/24
(58) Field of Classification Search .................... 607/18, 607/17, 24; 600/526, 547
See application file for complete search history.

(56) References Cited

U.S. PATENT DOCUMENTS

| 6,511,438 B2* | 1/2003 | Bernstein et al. | 600/526 |
| 6,561,986 B2* | 5/2003 | Baura et al. | 600/526 |
| 2002/0002389 A1* | 1/2002 | Bradley et al. | 607/8 |

* cited by examiner

*Primary Examiner* — Niketa Patel
*Assistant Examiner* — Michael D Abreu
(74) *Attorney, Agent, or Firm* — Procopio, Cory, Hargreaves & Savitch LLP (57) ABSTRACT

For cardiac rhythm management, a combination of cardiac pacing and a noninvasive heart monitoring is proposed for the determination of a set of programmable pacing parameters hemodynamically beneficial to the patient. The apparatus incorporates a cardiac pacemaker and a thoracic electrical bioimpedance (TEB) heart monitor. This combination allows the creation of a closed-loop system that obtains pacing parameter settings providing hemodynamically beneficial pacing therapy to the patient as determined by measuring and recording of stroke volume (SV), cardiac output (CO), and other indices of ventricular performance by the heart monitor during an optimization cycle automatically employing different permutations of values of pacing parameters such as atrioventricular delays, inter-atrial delay, inter-ventricular delay, or heart rate, that are sequentially programmed to the pacemaker. The hemodynamically beneficial permutation of pacing parameter values is determined from all recordings and programmed to the pacemaker for permanent or temporary pacing therapy.

9 Claims, 5 Drawing Sheets

METHOD AND APPARATUS FOR AUTOMATIC DETERMINATION OF HEMODYNAMICALLY OPTIMAL CARDIAC PACING PARAMETER VALUES

RELATED APPLICATION

The present application is a Divisional of co-pending U.S. patent application Ser. No. 10/402,230 filed on Mar. 27, 2003, the entire disclosure of which is incorporated herein by reference.

BACKGROUND

1. Field of the Invention

This invention relates generally to cardiac rhythm management, and more particularly to a combination of cardiac pacing and optimizing pacing parameter values.

2. Related Art

Dual-chamber pacemakers are used increasingly in patients with varying degrees of heart block, symptomatic bradydysrhythmias, and drug-refractory cardiomyopathy. Clinical benefits of the dual-chamber pacemaker include enhancement of forward blood flow, a feature that can alleviate symptoms of congestive heart failure (CHF), and prevention of atrial fibrillation caused by the atria contracting against a closed valve (Gadler F, Linde C, Darpo B. Modification of atrioventricular conduction as adjunct therapy for pacemaker-treated patients with hypertrophic obstructive cardiomyopathy. Eur Heart J 1998; 19:132-138).

Dual-chamber pacing can improve hemodynamics in some patients with dilated cardiomyopathy, likely by abolishing diastolic mitral regurgitation through the establishment of mechanical atrial and ventricular synchrony (Nishimura R, Hayes D, Holmes D, Tajik A. Mechanism of hemodynamic improvement by dual-chamber pacing for severe left ventricular dysfunction: An acute Doppler and catheterization hemodynamic study. J Am Coil Cardiol 1995; 25:281-288). Despite the benefit of optimization of atrioventricular (AV) delay, dual-chamber pacemakers often are left at the default value, which the manufacturer sets to approximately 170 milliseconds (Kindermann M, Frohlig G, Doerr T, Schieffer H. Optimizing the AV delay in DDD pacemakers with high degree AVE block: Mitral valve Doppler versus impedance cardiography. Pacing Clin Electrophysiol 1997; 20: 2453-2462). It is the consensus of independent researchers that optimization of AV interval is not routinely performed. Procedures for pacemaker optimization, specifically obtaining stroke volume measurements at different AV intervals by aortic Doppler echocardiography, traditionally have been observer-dependent, time-consuming, and costly.

The goal of AV optimization is the synchronization of the completion of end-diastolic filling exactly at the onset of left ventricular contraction. Obviously, to accomplish this objective, precise physiological measurements of the events of the cardiac cycle must be obtained. Because of a wide range of cardiac conditions, status of the ventricles, and cardioactive medications, each and every patient is unique. Leonelli et al. (Leonelli F, Wang K, Youssef M, Brown D. Systolic and diastolic effects of variable atrioventricular delay in patients with pacemakers. Eur Heart J 1995; 15:1431-1440) observed that an optimal setting of the AV delay value improved stroke volume up to 42%.

Another application of cardiac pacemakers has recently been discovered: Recent reports are suggesting that biventricular pacing may offer some important options in the treatment of patients with congestive heart failure (CHF). A significant percentage of patients with CHF have conduction abnormalities on EGG. These conduction abnormalities result in abnormal activation of ventricular myocardium and asynchronous activation of the atrial and ventricular chambers. Biventricular pacing attempts to activate the right and left ventricles simultaneously, producing what is termed "ventricular resynchronization".

Studies have confirmed acute and short-term hemodynamic benefits of biventricular pacing. In addition, studies have documented improvement in the functional status of patients with CHF. Larger, prospective studies investigating the beneficial effects of biventricular pacing and its clinical implications are currently underway.

In addition to the symptomatic and functional improvements, other important changes have been noted in CHF patients treated with biventricular pacing. Parameters of cardiac function such as left ventricular dimensions and myocardial performance index have improved markedly. Elevated plasma norepinephrine levels, which are associated with increased mortality in CHF, improve in biventricular pacing. Decreased heart rate variability, also associated with increased risk of sudden death in CHF, has been shown to improve. These findings have lead investigators to hypothesize the potential for biventricular pacing to improve survival. This being said, no trial to date has demonstrated a survival benefit to biventricular pacing. Furthermore, no studies are known that investigate the effects, and potential benefits, of biventricular pacing forcing a small delay between right ventricular and left ventricular contraction, or vice versa.

When optimizing the AV delay, or any other delay such as a delay between the contraction of right and left ventricles, it must be tailored to the individual patient. For almost two decades, stroke volume measurements by means of thoracic electrical bioimpedance (TEB) have been favorably considered for optimal determination of pacemaker settings. More recently, Hayes et al. (Hayes D, Hayes S, Hyberger L. Atrioventricular interval optimization technique: Impedance measurements vs Echo/Doppler. Presented at the North American Society for Pacing & Electrophysiology's 19th Annual Scientific Sessions, San Diego, Calif., May 9, 1998) reported that the noninvasive hemodynamic monitoring with TEB permits determination of optimal AV delay within 15 minutes in any clinical settings.

Despite promising benefits to the patient, the utilization of thoracic electrical bioimpedance (TEB), as with any other aforementioned method, has not been established as a standard optimization procedure for the setting of parameter values of dual-chamber pacemakers. Apparently, the TEB procedure, applied during pacemaker follow-up, is time-consuming and requires active involvement of the physician during the entire optimization period.

Rate-responsive cardiac pacemakers address the adaptation of the pacing rate according to the physiological demands related to the activity of the pacemaker patient. Sensors determine, for example, posture and movement of the patient, or respiration, characterized by respiration rate and tidal volume, and even stroke volume by measurement of thoracic electrical bioimpedance. The pacemaker adapts the pacing rate depending on the information obtained by the sensors and processed usually by the pacemaker. The pacemaker's rate adapted to the patient's activity is not within the scope of the aforementioned optimization techniques, and the invention.

SUMMARY

In one aspect, the method and apparatus defined in the appended claims incorporates a cardiac pacemaker and thoracic electrical bioimpedance (TEB) measuring approach.

With this combination of a diagnostic (TEB) and therapeutic method and apparatus (pacemaker) a closed-loop system is created to obtain, within its confines, an optimal or beneficial setting of pacing parameter values.

In one embodiment, a specific optimization cycle, triggered by an operator or upon the expiration of a preset time interval, automatically permutates the values of one or more pacing parameters, such as AV delays, inter-atrial delay, inter-ventricular delay, or heart rate, within operator-defined ranges, and determines at each permutation of parameter values hemodynamic parameters, such as stroke volume (SV), cardiac output (CO), ejection fraction (EF), and other indices of ventricular performance.

The operator defines one or more pacing parameters, such as atrioventricular delays, inter-atrial delay, inter-ventricular delay, or heart rate, which are subject to variation during an optimization cycle. Furthermore, the operator defines a variation range for values of each pacing parameter and a variation step width for stepping through the variation range during the optimization cycle. The number of pacing parameters subject to variation and the number of applicable variation steps for each parameter determine the number of permutations of pacing parameter values and, thus, the sequence of the optimization cycle. Each permutation of pacing parameter values is applied, for example, for a pre-defined period in the range of 30 to 120 seconds. The pacing parameter value, which results in the maximum value of a hemodynamic parameter, or a combination thereof, is the output of the optimization cycle and adapted by the cardiac pacemaker for further stimulation.

The hemodynamic measurements are performed utilizing the apparatus and method of Bernstein and Osypka as described in detail in European patent application No. 02007310.2 of the present applicant, Osypka Medical GmbH, Berlin, for APPARATUS AND METHOD FOR DETERMINING AN APPROXIMATE VALUE OF THE STROKE VOLUME AND THE CARDIAC OUTPUT OF THE HEART, filed concurrently herewith (in the following referred to as the Osypka EP application No. 02007310.2), the entire disclosure of which is incorporated herein by reference.

The optimization cycle automatically executed for a number of permutations of pacing parameter values to obtain maximal left-ventricular function enhances significantly the time-efficacy of an otherwise cumbersome and time-consuming, but nevertheless beneficial method. This automatic optimization method can be applied during pacing system analysis (PSA) prior to permanent pacemaker implantation, during temporary pacing following cardiothoracic surgery, during follow-up of a patient with an implantable pacemaker, or during the investigation of efficacy of pacing algorithms for patients undergoing treatment for congestive heart failure (CHF).

Other objects, features and advantages of the invention will become apparent from the following description of some exemplary embodiments of the invention.

BRIEF DESCRIPTION OF THE DRAWINGS

The details of the present invention, both as to its structure and operation, may be gleaned in part by study of the accompanying drawings, in which like reference numerals refer to like parts, and in which.

DETAILED DESCRIPTION

Certain embodiments as disclosed herein provide for a method and system for automatic determination of hemodynamically desirable cardiac pacing parameter values. Embodiments are employed, for example, but not limited to, in a Pacing System Analyzer (PSA) or external cardiac pulse generator (temporary cardiac pacemaker).

After reading this description it will become apparent to one skilled in the art how to implement the invention in various alternative embodiments and alternative applications. However, although various embodiments of the present invention will be described herein, it is understood that these embodiments are presented by way of example only, and not limitation.

Figure 1:
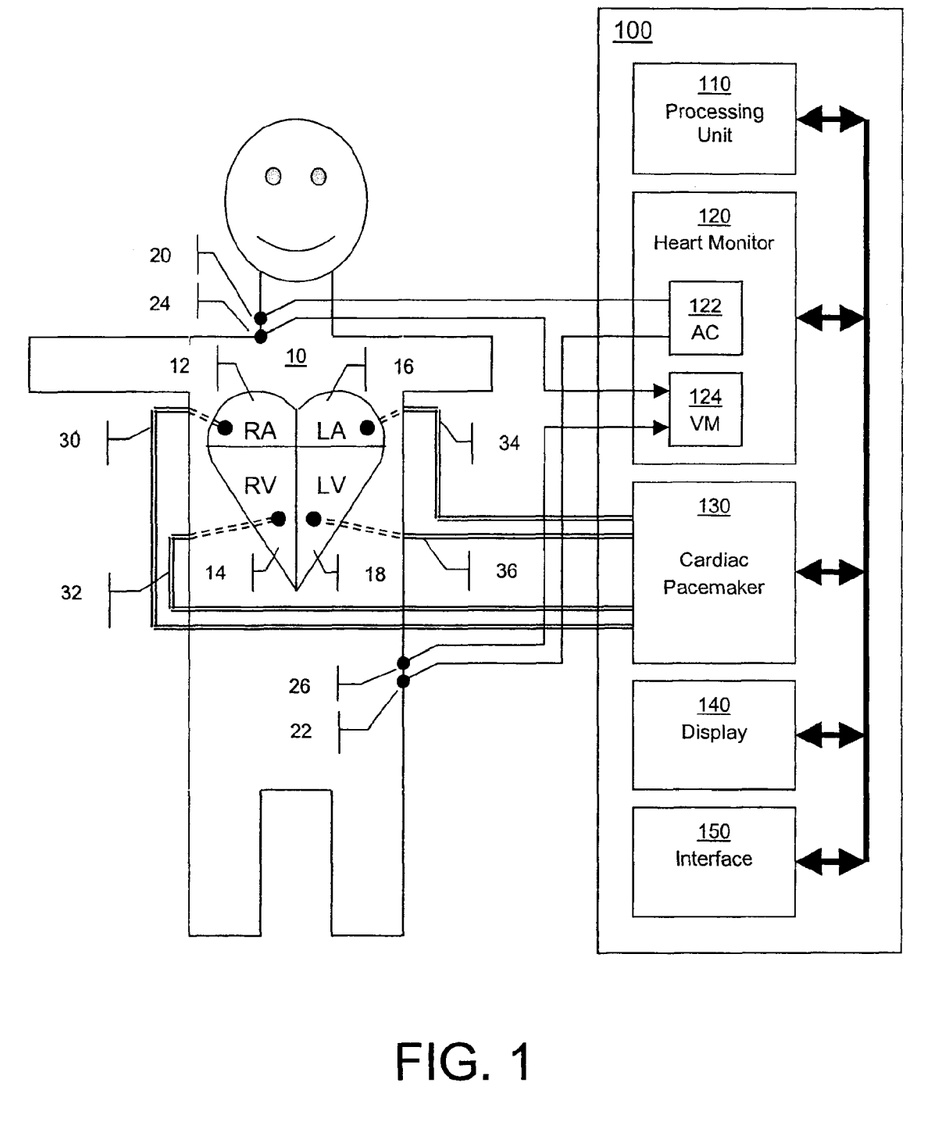
FIG. 1 illustrates a first embodiment where the optimization apparatus and the cardiac pacemaker are integrated into one system.

FIG. 1 shows a patient 10 and his stylized heart containing four chambers: right atrium 12, right ventricle 14, left atrium 16 and left ventricle 18. In the preferred embodiment shown, surface ECG-type electrodes as part of an electrode array are attached to the patient's right side of neck and the left side of lower thorax. The outer surface electrodes 20, 22 are connected to the alternating current (AC) source 122 of the heart monitor 120, which is part of the optimization apparatus 100. The inner surface electrodes 24, 26 are connected to the voltmeter 124 of the heart monitor 120. The heart monitor 120 determines from the ratio of the AC applied by 122 and the voltage measured by 124 the thoracic electrical bioimpedance.

Alternatively, the heart monitor 120 determines from the reciprocal ratio of the AC applied by 122 and the voltage measured by 124 the thoracic electrical bioadmittance. This method is described in the above-mentioned Osypka EP application No. 02007310.2 which is herein incorporated by reference, which describes how the continuous measurement of thoracic electrical bioimpedance is used to determine stroke volume and cardiac output.

Alternatively, the thoracic electrical bioimpedance (or bioadmittance) can be measured using different electrode configurations, including a second electrode array, and electrodes located on an esophageal catheter/probe, all described in Osypka EP Application No. 02007310.2.

Furthermore, a cardiac pacemaker 130 integrated into 100 is connected to at least two heart chambers of right atrium (RA) 12, right ventricle (RV) 14, left atrium (LA) 16 and left ventricle (LV) 18. In the event the optimization apparatus 100 is used for pacing system analysis, the connection of the heart chambers and the apparatus is accomplished by permanent pacing leads (indicated by the dashed part of the connection 30 to the right atrium 12, the dashed part of the connection 32 to the right ventricle 14, the dashed part of the connection 34 to the left atrium 16, and the dashed part of the connection 36 to the left ventricle 18), all of which are later connected to an implantable pacemaker, and extension cables (indicated by the solid part of the connection 30 to the right atrium 12, the solid part of the connection 32 to the right ventricle 14, the solid part of the connection 34 to the left atrium 16, and the solid part of the connection 36 to the left ventricle 18).

The processing unit 110 of the optimization apparatus 100 processes the permutations of the pacing parameter values, i.e. the pacing parameter values applied by cardiac pacemaker 130, such as heart rate (pacing or stimulation rate output by the pacemaker), and atrioventricular (AV), inter-atrial (AA) and inter-ventricular (also known as bi-ventricular) (VV) delays, and records the corresponding measurements of stroke volume, cardiac output, ejection fraction (EF) and other indices of ventricular performance in a data storage module of the processing unit. An input device (not illustrated) is connected to the optimization apparatus for operator input of pacing parameters, variation ranges, and variation step widths to define an optimization cycle.

According to one embodiment, a specific optimization cycle, triggered by an operator or upon the expiration of a preset time interval, automatically varies one or more pacing parameters, such as AV delays, inter-atrial delay, inter-ventricular delay, or heart rate, within operator-defined ranges, and determines at each parameter setting hemodynamic parameters, such as stroke volume (SV), cardiac output (CO), and other indices of ventricular performance. Each application of set pacing parameters is applied, for example, but not limited to, for a period in the range of 30 to 120 seconds. The processing unit records the hemodynamic parameters with each permutation of pacing parameter values, and, upon completion of the optimization cycle, indicates the permutation of pacing parameter values leading to optimal stroke volume, cardiac output and other indices of ventricular performance.

The results are numerically of graphically shown on a display 140. In the event the display 140 features a touch screen, patient demographic parameters, such as name, age, and weight, can be entered via the touch screen. Alternatively, the optimization apparatus 100 features an interface 150 to a keyboard or a port allowing communication with peripheral devices.

Typical applications for the aforementioned preferred embodiment are, but not limited to, Pacing System Analysis (PSA) with permanent pacing leads connected to the apparatus, Temporary Pacing (T.P.) after cardiac surgery using temporary myocardial pacing leads (heart wires), and temporary pacing treatment of congestive heart failure (CHF Pacing).

Figure 2:
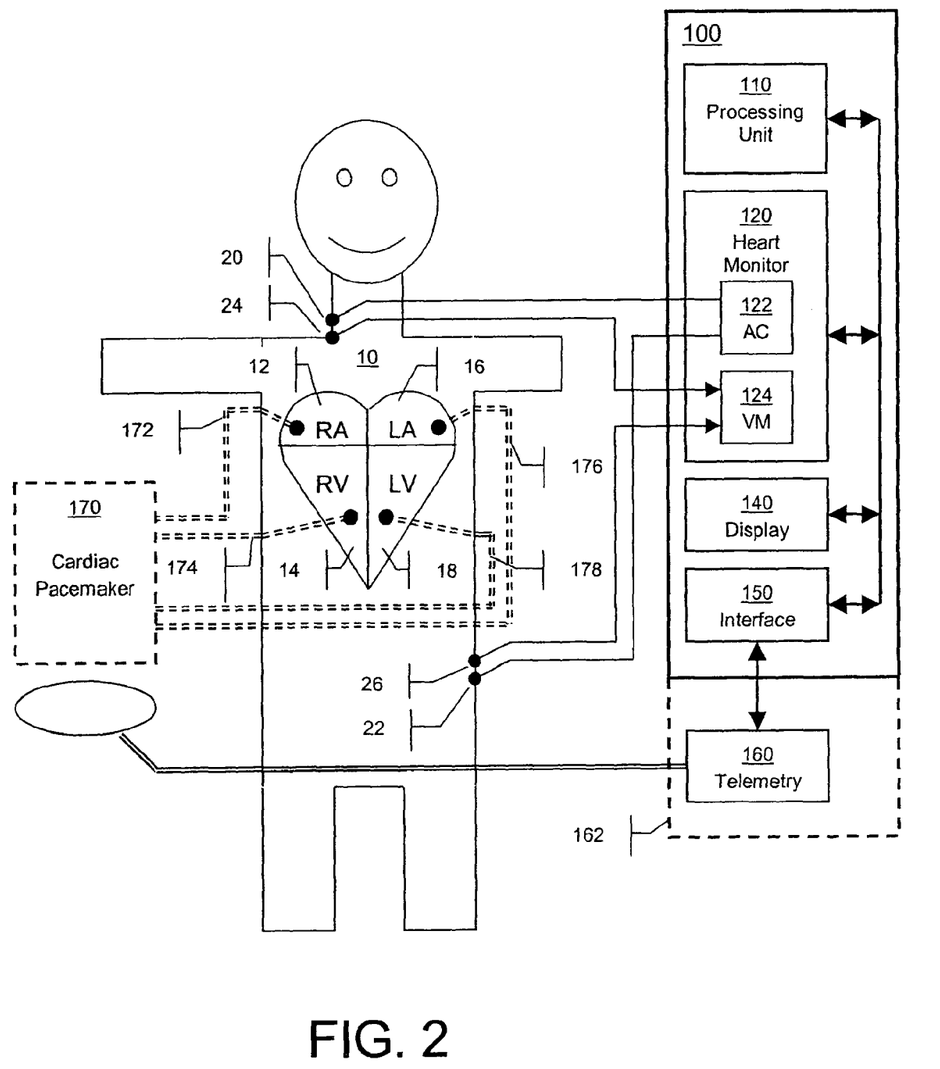
FIG. 2 illustrates a second embodiment where the optimization apparatus and the cardiac pacemaker are separate units.

FIG. 2 illustrates a second embodiment which employs, for example, but not limited to, in a combination of a permanent cardiac pacemaker and a corresponding external programmer for permanent pacemakers, with or without an Pacing System Analyzer (PSA) integrated into the programmer. With regards to temporary pacing, this embodiment is employed, for example, but not limited to, in a combination of a temporary cardiac pulse generator (temporary cardiac pacemaker) and a hemodynamic measurement unit interfacing with the pulse generator.

FIG. 2 shows the patient 10 after implantation of a permanent cardiac pacemaker 170. The cardiac pacemaker 170 is connected to at least two heart chambers of right atrium (RA) 12 via a permanent pacing lead 172, right ventricle (RV) 14 via a permanent pacing lead 174, left atrium (LA) 16 via a permanent pacing lead 176, and left ventricle (LV) 18 via a permanent pacing lead 178. FIG. 2 shows the connections from the permanent cardiac pacemaker to the heart chambers, i.e. the pacing leads, by dashed lines to indicate that these pacemaker leads are implanted into the patient and, thus, not part of the optimization apparatus.

The optimization apparatus 100 incorporates a heart monitor 120, a display 140, an interface 150, all controlled by a control module of processing unit 110. The optimization apparatus communicates with the permanent cardiac pacemaker through the interface 150 and an external pacemaker telemetry unit 160, which, for example, is provided by the manufacturer of the permanent cardiac pacemaker 170. Alternatively, the telemetry unit 160 is integrated into the optimization apparatus, which is indicated by the dashed lines 162 extending the apparatus 100.

The communication between the optimization apparatus 100 and the permanent pacemaker 170 is important to synchronize any new permutation of pacing parameter values with the corresponding hemodynamic parameter measurements performed by the optimization apparatus 100. If no communication can be established, then, at least, the physician programming the cardiac pacemaker 170 and operating the optimization apparatus 100 must know and record the related set pacing and measured hemodynamic parameters.

In the embodiment shown, surface ECG-type electrodes as part of an electrode array are attached to the patient's right side of neck and the left side of lower thorax. The outer surface electrodes 20, 22 are connected to the alternating current (AC) source 122 of the heart monitor 120, which is part of the optimization apparatus 100. The inner surface electrodes 24, 26 are connected to the voltmeter 124 of the heart monitor 120. The heart monitor 120 determines from the ratio of the AC applied by 122 and the voltage measured by 124 the thoracic electrical bioimpedance.

Alternatively, the heart monitor 120 determines from the reciprocal ratio of the AC applied by 122 and the voltage measured by 124 the thoracic electrical bioadmittance. The above-mentioned Osypka EP application No. 02007310.2, which is herein incorporated by reference, describes how the continuous measurement of thoracic electrical bioimpedance is used to determine stroke volume and cardiac output.

Alternatively, the thoracic electrical bioimpedance (or bioadmittance) can be measured using different electrode configurations, including a second electrode array, and electrodes located on an esophageal catheter/probe, all described in the above-mentioned Osypka EP application No. 02007310.2.

Typical applications for the aforementioned preferred embodiment are, but not limited to, the examination of a pacemaker patient upon a follow-up visit, and hemodynamic optimization during temporary pacing after cardiothoracic surgery.

Figure 3:
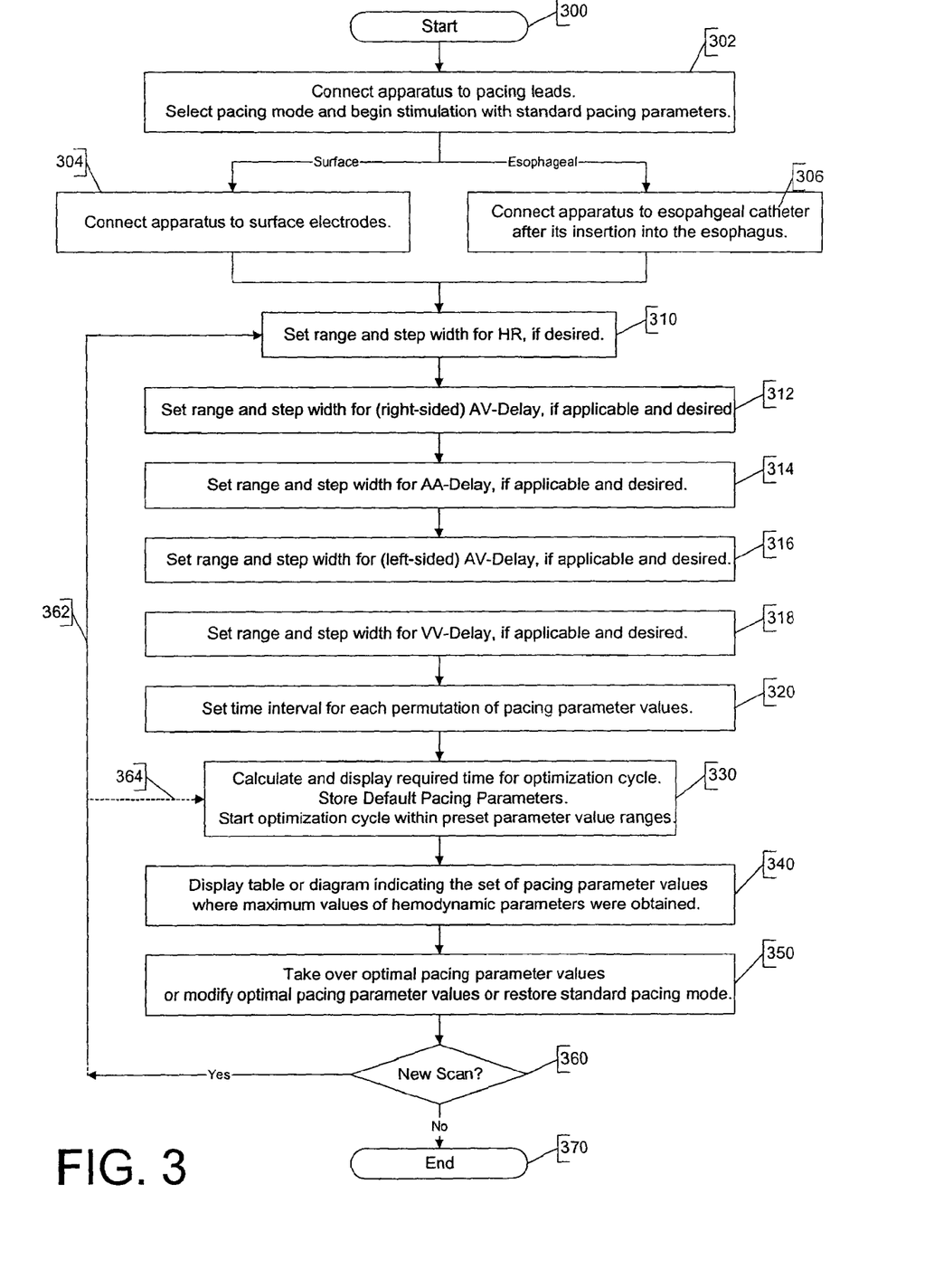
FIG. 3 illustrates a flowchart about the various steps of the automatic optimization process.

FIG. 3 illustrates a flowchart about the various steps of the optimization process.

FIG. 3 illustrates a generalized flowchart about the preparation steps of the optimization cycle, i.e. the process which executes the defined number of permutations of pacing parameter values and leads to a permutation of pacing parameter values providing the patient with maximum stroke volume, cardiac output, and other indices of ventricular performance, or any combination thereof.

Upon Start 300 of the procedure, the patient is at rest. In order to provide immediate pacing therapy, if required, the pacemaker, which mayor may not be an integral part of the optimization apparatus, is connected to the pacing leads. In the event of pacemaker patient follow-up, the pacing leads are already part of the implanted pacemaker system. The cardiac pacemaker is stimulating on demand, or, asynchronously to the heart rhythm, with a fixed pacing rate 302. The physician decides whether the heart monitor integrated into the optimization apparatus utilizes the transthoracic electrical bioimpedance approach, where the alternating current is applied, and the resulting voltage measured, through surface electrodes 304. Alternatively, in patients who are already intubated, the esophageal approach is utilized, where the alternating current is applied, and the resulting voltage measured, through electrodes located on an esophageal catheteprobe 306.

The operator defines the pacing parameter, namely the heart rate 310, defines or determines the variation range for the value of the pacing parameter, and the variation step width for stepping through the variation range of the heart rate 310. For example, the later optimization cycle for the heart rate shall begin with a heart rate of 70, then increase the heart rate by 5 beats per minute (variation step width=5), until a heart rate of 80 beats per minute. Alternatively, the heart rate can be set to a fixed value, with no range to vary.

The operator determines the variation range, and the variation step width, for the atrioventricular (AV) delay 312. In this context, with AV-Delay meant to be the right-sided AV-Delay, the time delay applied between sensing or stimulation in the right atrium and stimulation in the right ventricle. For example, the later optimization cycle of the optimization cycle shall begin with an AV-Delay of 150 ms, then increase the AV-Delay by 50 ms (variation step width=50 ms), until an AV-Delay of 250 ms is reached. Alternatively, the AV-Delay can be set to a fixed value, with no range to vary.

The operator determines the variation range, and the variation step width, for the inter-atrial (M) delay 314. In this context, with M-Delay meant to be the time delay applied between sensing or stimulation in the right atrium and stimulation in the left atrium. For example, the later optimization cycle shall begins with an M-Delay of 0 ms, then increase the M-Delay by 5 ms (variation step width=5 ms), until an M-Delay of 10 ms is reached. Alternatively, the M-Delay can be set to a fixed value, for example to 0 ms, with no range to vary.

The operator determines the variation range, and the variation step width, for the left-sided atrioventricular (LAV) delay 316. In this context, LAV-Delay is meant to be the left-sided AV-Delay, the time delay applied between sensing or stimulation in the left atrium and stimulation in the left ventricle. For example, the later optimization cycle shall begin with an LAV-Delay of 150 ms, then increase the LAV-Delay by 50 ms (variation step width=50 ms), until an LAV-Delay of 250 ms is reached. Alternatively, the LAV-Delay can be set to a fixed value, with no range to vary.

The operator determines the variation range, and the variation step width, for the inter-ventricular (VV) delay 314. In this context, with VV-Delay meant to be the time delay applied between sensing or stimulation in the right ventricle and stimulation in the left ventricle. For example, the later optimization cycle shall begin with an W-Delay of 0 ms, then increase the W-Delay by 5 ms (variation step width=5 ms), until a VV-Delay of 10 ms is reached. Alternatively, the VV-Delay can be set to a fixed value, for example to 0 ms, with no range to vary.

The operator determines the time interval between a variation of pacing parameter values 320. Upon a new permutation of pacing parameter values applied for therapy, the patient's hemodynamic response may take several cardiac cycles to establish. Consequently, the measurement of hemodynamic parameters immediately after the application of a new permutation of pacing parameter values may not reflect the actual hemodynamic changes induced by the changed pacing therapy. For example, within the later optimization cycle, each permutation of pacing parameters shall be held constant for 30 seconds, and measurements of the first cardiac cycles upon each permutation applied may be ignored.

The order of setting the variation ranges and variation step width for heart rate 310, M-Delay 314, AV-Delay 316, VV-Delay 318 and time interval 320 is arbitrary and can be changed. When setting the variation ranges and variation step widths, as well as the time interval, the physician must take into account that there is a compromise between wide ranges and close step widths of pacing parameters values, and the time the automatic optimization cycle will take, that is, the time the patient can be exposed to the measurements.

Upon set pacing parameter variation ranges and variation step widths, an optimization module or optimization means of the optimization apparatus calculates and displays the time required for the automatic optimization cycle or scan 330. Depending on the calculated time and the time restrictions the patient's state of heath or situation mandates, the physician is able to readjust the previously set ranges and step widths. In the event the time required for the automatic optimization cycle is acceptable, the physician confirms the start of the automatic optimization cycle through the predefined pacing parameter variation ranges with the predefined variation step widths. The optimization apparatus stores the default set of pacing parameters prior to the start of the automatic optimization cycle, which can be reset upon termination of the automatic optimization cycle.

Upon termination of the optimization cycle 340, the hemodynamic parameter values obtained are displayed with the corresponding permutations of pacing parameter values. The results are displayed in form of a table, with the permutation of pacing parameter values leading to maximum stroke volume, cardiac output, ejection fraction and other indices of ventricular performance, marked. Alternatively, two- or three-dimensional graphs are utilized to display a spectrum of pacing parameter value sets and their therapeutical impact on this particular patient.

The physician then has the choice of applying a preferred permutation of pacing parameter values parameter set, or a modification of it, for therapy, or return to the previously used and stored default set of pacing parameter values 350.

During pacing system analysis, any new placement of permanent pacing leads may suggest the execution of a new automatic optimization cycle 360. The physician has the option to reprogram the previously set pacing parameter value ranges and variation step widths 362, or initiate a new automatic optimization cycle with the pacing parameter ranges and step widths previously used 364. Alternatively, the pacemaker optimization is ended 370.

Figure 4:
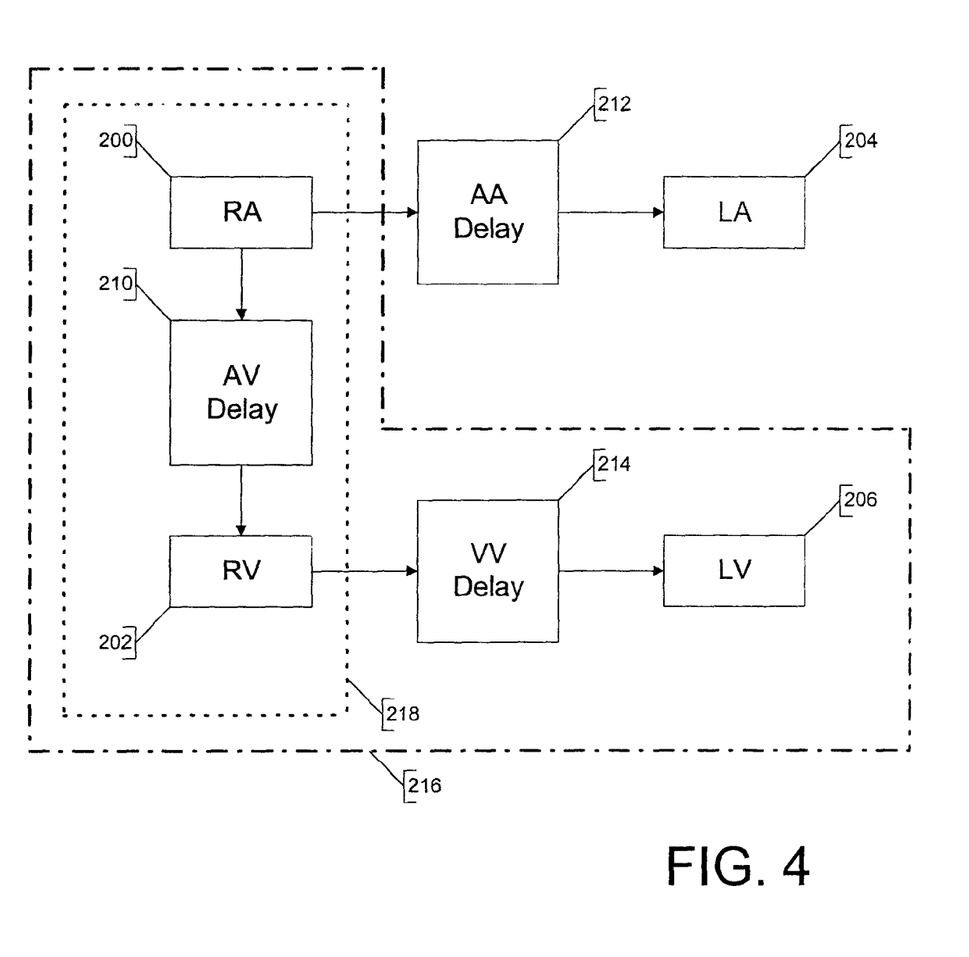
FIG. 4 illustrates schematically the sensing and pacing sequence of the AVV-Mode.

FIG. 4 illustrates schematically the sensing and pacing sequence of the AVV-Mode.

FIG. 4 illustrates schematically the four heart chambers, and their respective sensing and pacing channels, right atrium (RA) 200, right ventricle (RV) 202, left atrium (LA) 204, and left ventricle (LV) 206, and a preferred operating mode (AVV Mode) of the cardiac pacemaker integrated into the optimization apparatus of FIG. 1. The pacemaker provides the functions to measure (sense) in each heart chamber the intrinsic activity, if extant, and to deliver a pacing stimulus.

In this context, the AV-Delay 210 is the programmed atrioventricular pacing interval, initiated by an atrial stimulus. The M Delay 212 is the programmed inter-atrial pacing interval, initiated by an atrial stimulus. The W-Delay 214 is the programmed inter-ventricular pacing interval, initiated by a ventricular stimulus.

FIG. 4 illustrates the most complex sensing and pacing therapy the AVV Mode provides. By disabling the pacing and sensing in specific heart chambers, the function of the complex cardiac is reduced to known and established pacing modes. In the event that no left-atrial sensing and stimulation is required, or applicable, the left-atrial channel is disabled. The three heart chambers remaining, and their respective sensing and pacing channels 216, right atrium (RA) 200, right ventricle (RV) 202, and left ventricle (LV) 206, are of particular interest in pacing therapy addressing congestive heart failure, known as biventricular, or CHF, pacing. To our knowledge, the application of a VV-Delay, which can assume a positive or negative value, has neither been published nor investigated.

Upon disabling pacing and sensing in the left ventricle, the two heart chambers remaining, and their respective sensing and pacing channels 218, right atrium (RA) 200, and right ventricle (RV) 202, are of particular interest in classical physiological pacing therapy, known as dual-chamber, or DDD, pacing.

Figure 5:
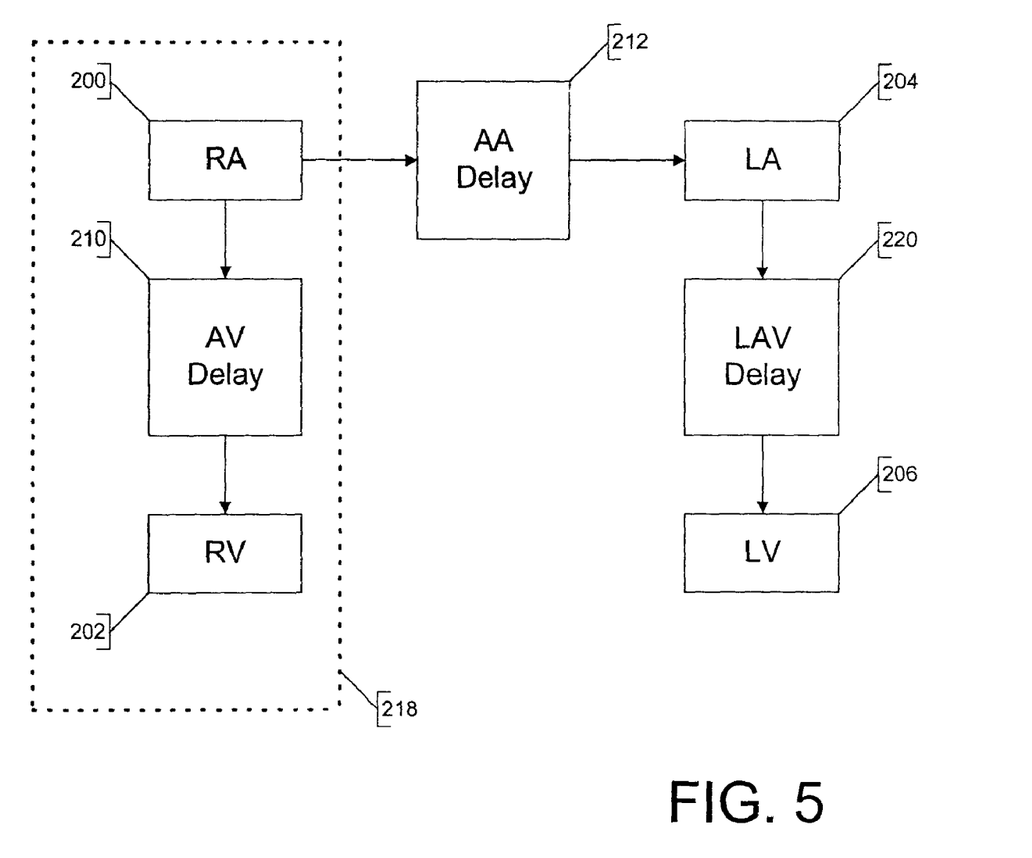
FIG. 5 illustrates the sensing and pacing sequence of the AVAV-Mode.

FIG. 5 illustrates schematically the sensing and pacing sequence of the AVAV-Mode.

FIG. 5 illustrates schematically the 4 heart chambers, and their respective sensing and pacing channels, right atrium (RA) 200, right ventricle (RV) 202, left atrium (LA) 204, and left ventricle (LV) 206, and another preferred operating mode (AVAV Mode) of the cardiac pacemaker integrated into the optimization apparatus of FIG. 1. The pacemaker provides the functions to measure (sense) in each heart chamber the intrinsic activity, if extant, and to deliver a pacing stimulus.

In this context, the AV-Delay 210 is the programmed right-sided atrioventricular pacing interval, initiated by an atrial stimulus. The AA Delay 212 is the programmed inter-atrial pacing interval, initiated by an atrial stimulus. The LAV-Delay 220 is the programmed left-sided atrioventricular pacing interval, initiated by a left-atrial stimulus.

Upon disabling pacing and sensing in the left atrium (LA) 204 and ventricle (LV) 206, the 2 heart chambers remaining, and their respective sensing and pacing channels 218, right atrium (RA) 200, and right ventricle (RV) 202, are of particular interest in classical physiological pacing therapy, known as dual-chamber, or DDD, pacing.

As indicated above, it is not only the stroke volume (SV) that can be used in order to optimize or improve the pacing parameters to be programmed onto the pacemaker. In general, most indices of left-ventricular cardiac performance may be suitable measures for optimization. The optimization apparatus measures in any event the heart rate (HR). Therefore, cardiac output (CO), instead of stroke volume (SV) may be used for the optimization process:

$$CO = \frac{SV \cdot HR}{1000}$$

where SV=Stroke Volume measured in milliliters (mL); CO=Cardiac Output measured in liters/minute; HR=Heart rate measured in beats/minute.

For the calculation of the stroke volume (SV), the following equation of the above-mentioned Osypka EP application No. 02007310.2 can be used (but not limited to):

$$SV = V_{EFF} \cdot C_1 \left( \frac{\left|\left(\frac{dZ(t)}{dt}\right)_{MIN}\right|}{Z_o} \right)^n \cdot \left(\frac{1}{T_{RR}}\right)^m \cdot T_{LVE}$$

or, in a special form with n=m=0.5 and $C_1=1$:

$$SV = V_{EFF} \cdot \sqrt{\frac{\left|\left(\frac{dZ(t)}{dt}\right)_{MIN}\right|}{Z_o}} \cdot F_{TC}$$

where $V_{EFF}$=Volume of electrically participating tissue; C=Constant;

$$\frac{\left|\left(\frac{dZ(t)}{dt}\right)_{MIN}\right|}{Z_0} = \text{Maximum rate of change of impedance;}$$

$Z_0$=Base impedance; $T_{RR}$=R–R interval; $T_{LVE}$=Left-ventricular ejection time; $FT_C$=Corrected flow time; $FT_C=T_{LVE}/T_{RR}$ $V_{EFF}$ is a factor, which is typical for a particular patient, as it is derived, among other factors, from the patient's weight. $V_{EFF}$ is considered quasi-constant, because, according to the afore-mentioned Osypka EP application No. 02007310.2, $V_{EFF}$ depends also on the basic impedance $Z_0$. Considering the scope of possible applications, which require only several minutes for the optimization process, $Z_0$ varies, if at all, only by a small margin, and has practically no measurable influence on the SV or CO measured. If $Z_0$ and, consequently, $V_{EFF}$ being constant during the entire application for a particular patient, optimization without compromising accuracy can be achieved without knowledge of the patient's weight and, thus, $V_{EFF}$. For example, a "Stroke Index" $SI_1$ can be determined:

$$SI_1 = \left( \frac{\left|\left(\frac{dZ(t)}{dt}\right)_{MIN}\right|}{Z_o} \right)^n \cdot \left(\frac{1}{T_{RR}}\right)^m \cdot T_{LVE}$$

with 0.15≦n≦0.8 and 0 m 1.5 according to the aforementioned Osypka EP application.

A special "Stroke Index" $SI_1$ is determined with n=m=0.5:

$$SI_1 = \sqrt{\frac{\left|\left(\frac{dZ(t)}{dt}\right)_{MIN}\right|}{Z_o}} \cdot F_{TC}$$

The only shortcoming of such processing is that the user does not obtain (simple) absolute indication of the range in which patient's stroke volume is determined while the patient is undergoing the various permutations of pacing parameter values. The user, however, obtains relative values of "Stroke Indices" to compare.

With $Z_0$ considered constant, $Z_0$ may be omitted from the equation. The following simplified equation can be used to calculate another form of "Stroke Index" $SI_2$:

$$SI_2 = \left( \frac{\left|\left(\frac{dZ(t)}{dt}\right)_{MIN}\right|}{\Omega} \right)^n \cdot \left(\frac{1}{T_{RR}}\right)^m \cdot T_{LVE}$$

A special "Stroke Index" $SI_2$ is determined with n=m=0.5:

$$SI_2 = \sqrt{\frac{\left|\left(\frac{dZ(t)}{dt}\right)_{MIN}\right|}{\Omega}} \cdot F_{TC}$$

A further simplification but compromise in accuracy is to substitute corrected flow time $FT_C$ for left-ventricular ejection time (known also as systolic flow time) $T_{LVE}$ or even fully omit $FT_C$ or $T_{LVE}$. Accordingly, a "Stroke Index" $SI_3$ is determined:

$$SI_3 = \sqrt{\frac{\left|\left(\frac{dZ(t)}{dt}\right)_{MIN}\right|}{\Omega}}$$

Alternatively, a "Stroke Index" $SI_4$ is determined by normalizing $$\left|\left(\frac{dZ(t)}{dt}\right)_{MIN}\right|$$

through division by base impedance $Z_0$:

$$SI_4 = \sqrt{\frac{\left|\left(\frac{dZ(t)}{dt}\right)_{MIN}\right|}{Z_o}}$$

Stroke volume, cardiac output and the aforementioned "Stroke Indices" are, within their constraints, suitable hemodynamic parameters for determination of the optimal setting of pacing parameters. Alternatively, (left-ventricular) Ejection Fraction (EF) is an at least as suitable hemodynamic index for pacing parameter optimization.

In the above description, stroke volume is calculated based on bioimpedance (Z). Stroke volume (and the associated stroke indices) can alternatively be calculated based on bio-admittance (Y), as described in the above mentioned Osypka EP Application No. 02007310.2. Admittance is related to impedance as follows:

$$Y(t) = \frac{1}{Z(t)}$$

$$T_0 = \frac{1}{Z_0}$$

and $$\left(\frac{dY(t)}{dt}\right)_{MAX} \cong \frac{1}{Z_0^2}\left|\left(\frac{dZ(t)}{dt}\right)_{MIN}\right|$$

The stroke volume is therefore approximated to:

$$SV = V_{EFF} \cdot \sqrt{\frac{\left(\frac{dY(t)}{dt}\right)_{MAX}}{Y_0}} \cdot FT_C$$

The stroke volume equation in the previous paragraph which is based on bioadmittance can be used in exactly the same way as described above for bioimpedance to derive a similar stroke index $SI_Y$ based on bioadmittance:

$$SI_Y = \left(\frac{\left(\frac{dY(t)}{dt}\right)_{MAX}}{Y_0}\right)^n \cdot \left(\frac{1}{T_{RR}}\right)^m \cdot T_{LVE}$$

where $0.15 < n < 0.8$ and $0 \leq m \leq 1.5$. This eliminates the term $V_{EFF}$ from the SV equation above, since this term will be constant during an entire application for a particular patient. In view of the above relationship between $Y_0$ and $Z_0$, $V_{EFF}$ is dependent also on the basic admittance. If $Y_0$ and consequently $V_{EFF}$ are substantially constant during an entire application for a particular patient, optimization can the achieved without compromising accuracy and without knowledge of a patient's weight, using the above stroke index equation in which the term $V_{EFF}$ is eliminated.

A special stroke index is derived from the above equation with $n=m=0.5$, as follows:

$$SI_{Y1} = \sqrt{\frac{\left(\frac{dY(t)}{dt}\right)_{MAX}}{Y_0}} \cdot FT_C \quad (A)$$

If $Y_0$ is considered constant, it can be eliminated from the above equation. The following simplified equation can be used to calculate another form of stroke index, $SI_{Y2}$:

$$SI_{Y2} = \sqrt{\frac{\left(\frac{dY(t)}{dt}\right)_{MAX}}{\Omega}} \cdot FT_C \quad (B)$$

In order to produce a further simplification but a compromise in accuracy, the term $FT_c$ can be eliminated from either equation A or B above to produce the following alternative stroke indices:

$$SI_{Y3} = \sqrt{\frac{\left(\frac{dY(t)}{dt}\right)_{MAX}}{\Omega}} \text{ and } SI_{Y4} = \sqrt{\frac{\left(\frac{dY(t)}{dt}\right)_{MAX}}{Y_0}}.$$

The above description of the disclosed embodiments is provided to enable any person skilled in the art to make or use the invention. Various modifications to these embodiments will be readily apparent to those skilled in the art, and the generic principles described herein can be applied to other embodiments without departing from the spirit or scope of the invention. Thus, it is to be understood that the description and drawings presented herein represent a presently preferred embodiment of the invention and are therefore representative of the subject matter which is broadly contemplated by the present invention. It is further understood that the scope of the present invention fully encompasses other embodiments that may become obvious to those skilled in the art and that the scope of the present invention is accordingly limited by nothing other than the appended claims.

The invention claimed is:

1. A method of automatic determination of a multi-chamber cardiac pacemaker's pacing parameter values providing optimal pacing therapy for a specific patient, comprising:
receiving and storing an operator defined set of one or more programmable pacing parameters subject to variation, and operator defined parameter specific variation ranges and step widths of values for each pacing parameter, the pacing parameters being selected from the group consisting of atrioventricular delays (AV), inter-atrial delay (AA), inter-ventricular delay (VV), and heart rate (HR);

defining a predetermined optimization cycle comprising a sequence of different, permutations of pacing parameter values based on the number of different pacing parameters selected and the operator defined variation range and step width for each pacing parameter;

programming the different permutations of pacing parameter values one at a time to the pacemaker in accordance with the defined sequence of the optimization cycle;

taking hemodynamic measurements of heart performance parameters of a patient for each programmed permutation of pacing parameter values through non-invasive thoracic or esophageal measurements;

using the hemodynamic measurements to determine a stroke index (SI) of ventricular performance using the maximum rate of change of bioimpedance or bioadmittance, respectively;

the stroke index (SI) in case of bioimpedance (Z) including at least one of the following terms:

$$\frac{\left|\left(\frac{dZ(t)}{dt}\right)_{MIN}\right|}{Z_0}, \text{ or }$$

$$\left|\left(\frac{dZ(t)}{dt}\right)_{MIN}\right|$$

the stroke index in the case of bioadmittance (Y) including at least one of the following terms:

$$\frac{\left(\frac{dY(t)}{dt}\right)_{MAX}}{Y_0}, \text{ or } \left(\frac{dY(t)}{dt}\right)_{MAX}, \text{ where:}$$

$$\left|\left(\frac{dZ(t)}{dt}\right)_{MIN}\right|$$

is the maximum rate of change of impedance, $$\left(\frac{dY(t)}{dt}\right)_{MAX}$$

is the maximum rate of change of admittance,
$Z_0$ is the base impedance, and
$Y_0$ is the base admittance;

recording the stroke index determined for each permutation of applied pacing parameter values; and determining the optimal permutation of pacing parameter values for the patient from the stroke indices recorded for each permutation of pacing parameter values in the optimization cycle.

2. The method of claim 1, wherein the measurements of the stroke index (SI) are taken by left-sided atrioventricular (A-LV); right-sided atrioventricular (A-RV) or bi-sided atrioventricular (A-BV) stimulation.

3. The method of claim 1, further comprising programming the pacemaker with the determined optimal pacing parameter values.

4. The method of claim 1, further comprising synchronizing the hemodynamic measurements to the various permutations of pacing parameters values during the optimization cycle.

5. A method of automatic determination of a multi-chamber cardiac pacemaker's pacing parameter values for use in selecting pacing therapy for a specific patient without using a patient's weight in determining the pacing parameter values, comprising:

receiving and storing an operator defined set of one or more programmable pacing parameters subject to variation, and operator defined parameter specific variation ranges and step widths of values for each pacing parameter, the pacing parameters being selected from the group consisting of atrioventricular delays (AV), inter-atrial delay (AA), inter-ventricular delay (VV), and heart rate (HR);

defining a predetermined optimization cycle comprising a sequence of different, permutations of pacing parameter values based on the number of different pacing parameters selected and the operator defined variation range and step width for each pacing parameter;

programming the different permutations of pacing parameter values one at a time to the pacemaker in accordance with the defined sequence of the optimization cycle;

taking hemodynamic measurements of heart performance parameters of a patient through non-invasive thoracic or esophageal measurements for each programmed permutation of pacing parameter values;

using the hemodynamic measurements to calculate a stroke index (SI) of ventricular performance for each permutation of pacing parameter values, without using the patient's weight as an input in the stroke index calculation;

the stroke index (SI) in case of bioimpedance (Z) being calculated according to one of the following formulae:

$$SI = \left(\frac{\left|\left(\frac{dZ(t)}{dt}\right)_{MIN}\right|}{Z_0}\right)^n \cdot \left(\frac{1}{T_{RR}}\right)^n \cdot T_{LVE}$$

$$SI_1 = \sqrt{\frac{\left|\left(\frac{dZ(t)}{dt}\right)_{MIN}\right|}{Z_0}} \cdot FT_C, \quad SI_2 = \sqrt{\frac{\left|\left(\frac{dZ(t)}{dt}\right)_{MIN}\right|}{\Omega}} FT_C,$$

$$SI_3 = \sqrt{\frac{\left|\left(\frac{dZ(t)}{dt}\right)_{MIN}\right|}{\Omega}} \text{ and } SI_4 = \sqrt{\frac{\left|\left(\frac{dZ(t)}{dt}\right)_{MIN}\right|}{Z_0}},$$

with $$FT_C = \frac{T_{LVE}}{\sqrt{T_{RR}}}$$

the corrected flow time and with $\Omega$ being a constant,
and with
$0.15 < n < 0.8$ and $0 \leq m \leq 1.5$, where $$\left|\left(\frac{dZ(t)}{dt}\right)_{MIN}\right|$$

is the maximum rate of change of impedance,
$Z_0$ is the base impedance
$T_{RR}$ is the R-R interval, and
$T_{LVE}$ is the left-ventricular ejection time;

wherein the terms used to calculate the stroke indices in the foregoing formulae do not require input of the patient's weight as a variable;

recording the stroke index determined for each permutation of applied pacing parameter values; and determining the optimal permutation of pacing parameter values for the patient from the recorded stroke indices for each permutation of pacing parameter values in the optimization cycle, whereby the determination of pacing parameter values for a patient does not require input of the patient's weight.

6. Optimization apparatus for automatic determination of a multi-chamber cardiac pacemaker's pacing parameter values providing optimal pacing therapy, comprising a cardiac pacemaker;

a programmable processing unit configured to store an operator defined set of one or more programmable pacing parameters selected from the group comprising at least atrioventricular delay, inter-atrial delay, inter-ventricular delay, and heart rate, an input device connected to the programmable processing unit which receives operator input of a variation range and a step width of values within the range for each selected pacing parameter;

the processing unit comprising an optimization module which defines a predetermined optimization cycle comprising a sequence of different permutations of pacing parameter values based on the number of different pacing parameters selected and the operator defined variation range and step width for each selected parameter, the number of permutations in the optimization cycle being dependent on the number of pacing parameters selected and the variation range and step width for each selected parameter;

a control module linked to the pacemaker which inputs the defined sequence of permutations of pacing parameter values one at a time to the pacemaker until the predetermined optimization cycle is complete and all pre-defined permutations of pacing parameter values have been input in sequence to the pacemaker in accordance with the defined sequence of the optimization cycle, a heart monitor linked to the pacemaker which takes hemodynamic measurements of heart performance parameters of a patient in accordance with the operator defined sequence of the optimization cycle through non-invasive thoracic or esophageal measurements;

a processing module which uses the hemodynamic measurements to calculate a stroke index (SI) of ventricular performance for each permutation of pacing parameter values;

the stroke index (SI) calculation using the maximum rate of change of bioadmittance or bioimpedance, respectively;

the stroke index (SI) in case of bioimpedance (Z) including at least one of the following terms:

$$\frac{\left|\left(\frac{dZ(t)}{dt}\right)_{MIN}\right|}{Z_0}, \text{ or}$$

$$\left|\left(\frac{dZ(t)}{dt}\right)_{MIN}\right|$$

the stroke index in the case of bioadmittance (Y) including at least one of the following terms:

$$\frac{\left(\frac{dY(t)}{dt}\right)_{MAX}}{Y_o}, \text{ or}$$

$$\left(\frac{dY(t)}{dt}\right)_{MAX}, \text{ where:}$$

$$\left|\left(\frac{dZ(t)}{dt}\right)_{MIN}\right|$$

is the maximum rate of change of impedance, $$\left(\frac{dY(t)}{dt}\right)_{MAX}$$

is the maximum rate of change of admittance, $Z_0$ is the base impedance, and $Y_0$ is the base admittance;

a data storage module configured to record the measurements of stroke indices for each permutation of applied pacing parameter values throughout the entire predetermined optimization cycle, and a display module configured to display the recorded stroke indices along with the corresponding permutations of pacing parameter values for the entire optimization cycle, whereby an operator can determine any optimum stroke index and the optimal permutation of pacing parameter values corresponding to that index, and the control module further being configured to program the pacemaker with the so found optimal permutation of pacing parameter values.

7. The apparatus of claim 6, wherein the processing module calculates the stroke index for each permutation of pacing parameter values for a patient without using a patient's weight as an input in the stroke index calculation.

8. The method of claim 1, wherein the hemodynamic measurements are used to determine a stroke index for each programmed set of pacing parameter values for a patient without using a patient's weight in determining the stroke index, and the optimal set of pacing parameter values is selected for a specific patient based on the recorded stroke indices for each set of pacing parameter values for the specific patient independent of the patient's weight.

9. A method of automatic determination of a multi-chamber cardiac pacemaker's pacing parameter values for use in selecting pacing therapy for a specific patient without using a patient's weight in determining the pacing parameter values, comprising:

receiving and storing an operator defined set of one or more programmable pacing parameters subject to variation, and operator defined parameter specific variation ranges and step widths of values for each pacing parameter, the pacing parameters being selected from the group consisting of atrioventricular delays (AV), inter-atrial delay (AA), inter-ventricular delay (VV), and heart rate (HR);

defining a predetermined optimization cycle comprising a sequence of different, permutations of pacing parameter values based on the number of different pacing parameters selected and the operator defined variation range and step width for each pacing parameter;

programming the different permutations of pacing parameter values one at a time to the pacemaker in accordance with the defined sequence of the optimization cycle;

taking hemodynamic measurements of heart performance parameters of a patient through non-invasive thoracic or esophageal measurements for each programmed permutation of pacing parameter values;

using the hemodynamic measurements to calculate a stroke index (SI) of ventricular performance for each permutation of pacing parameter values, without using the patient's weight as an input in the stroke index calculation;

the stroke index in the case of bioadmittance (Y) being calculated according to one of the following formulae:

$$SI_Y = \left(\frac{\left(\frac{dY(t)}{dt}\right)_{MAX}}{Y_0}\right)^n \cdot \left(\frac{1}{T_{RR}}\right)^m \cdot T_{LVE}$$

$$SI_{Y1} = \sqrt{\frac{\left(\frac{dY(t)}{dt}\right)_{MAX}}{Y_0}} \cdot FT_C, \quad SI_{Y2} = \sqrt{\frac{\left(\frac{dY(t)}{dt}\right)_{MAX}}{\Omega}} \cdot FT_C$$

$$SI_{Y3} = \sqrt{\frac{\left(\frac{dY(t)}{dt}\right)_{MAX}}{\Omega}} \quad \text{and} \quad SI_{Y4} = \sqrt{\frac{\left(\frac{dY(t)}{dt}\right)_{MAX}}{Y_0}},$$

with $$FT_C = \frac{T_{LVE}}{\sqrt{T_{RR}}}$$

the corrected flow time and with $\Omega$ being a constant, and with
$0.15 < n < 0.8$ and $0 \leq m \leq 1.5$, where $$\left(\frac{dY(t)}{dt}\right)_{MAX}$$

is the maximum rate of change of admittance
$Y_0$ is the base admittance
$T_{RR}$ is the R-R interval, and
$T_{LVE}$ is the left-ventricular ejection time;

wherein the terms used to calculate the stroke indices in the foregoing formulae do not require input of the patient's weight as a variable;

recording the stroke index determined for each permutation of applied pacing parameter values; and determining the optimal permutation of pacing parameter values for the patient from the recorded stroke indices for each permutation of pacing parameter values in the optimization cycle, whereby the determination of pacing parameter values for a patient does not require input of the patient's weight.

\* \* \* \* \*